United States Patent
Hansen et al.

(10) Patent No.: US 7,309,024 B2
(45) Date of Patent: Dec. 18, 2007

(54) WICK ASSEMBLY FOR DISPENSING A VOLATILE LIQUID FROM A CONTAINER AND METHOD OF ASSEMBLING SAME

(75) Inventors: Jeffory S. Hansen, Kansasville, WI (US); Kara L. Lakatos, Racine, WI (US); Jeffrey J. Christianson, Oak Creek, WI (US); Mary Beth Adams, Antioch, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 168 days.

(21) Appl. No.: 10/609,843

(22) Filed: Jun. 30, 2003

(65) Prior Publication Data

US 2004/0262420 A1    Dec. 30, 2004

(51) Int. Cl.
  B05B 17/04    (2006.01)
  A61L 9/04    (2006.01)
  A24F 25/00    (2006.01)

(52) U.S. Cl. .............. 239/4; 239/44; 239/6; 239/34; 239/40; 239/50; 239/37

(58) Field of Classification Search ............... 239/44, 239/6, 34, 37, 41, 42, 43, 50, 4, 40; 392/392, 392/394, 395, 390
See application file for complete search history.

(56) References Cited

U.S. PATENT DOCUMENTS

| | | |
|---|---|---|
| 1,911,871 A | 5/1933 | Anderson |
| 2,435,811 A | 2/1948 | Waters ................ 240/10 |
| 2,557,501 A | 6/1951 | Fusay et al. ............. 21/119 |
| 2,754,554 A | 7/1956 | Mills |
| 2,764,789 A | 10/1956 | Zelenka ................ 21/74 |
| 2,828,953 A | 4/1958 | Hartmann ............. 261/30 |
| 2,867,866 A | 1/1959 | Steele |
| 3,080,624 A | 3/1963 | Weber, III ............ 21/120 |
| 3,587,968 A | 6/1971 | Balland et al. .......... 239/47 |
| 3,633,881 A | 1/1972 | Yurdin ................. 261/24 |
| 3,748,464 A | 7/1973 | Andeweg ............ 240/108 R |
| 3,749,904 A | 7/1973 | Graff ................. 240/10 B |
| 3,761,702 A | 9/1973 | Andeweg ............. 240/2 R |
| 3,790,081 A | 2/1974 | Thornton et al. |
| 3,890,085 A | 6/1975 | Andeweg ............. 431/125 |
| 3,923,458 A | 12/1975 | Moran ................ 21/74 R |
| 3,948,445 A | 4/1976 | Andeweg ............. 239/53 |
| 3,990,848 A | 11/1976 | Corris |
| 3,993,444 A | 11/1976 | Brown |
| 4,035,451 A | 7/1977 | Tringali |
| 4,166,087 A | 8/1979 | Cline et al. |

(Continued)

FOREIGN PATENT DOCUMENTS

AU    664685    11/1995

(Continued)

OTHER PUBLICATIONS

"Inglow™ Candle Company" www.inglowcandle.com (2002).

(Continued)

*Primary Examiner*—Davis Hwu

(57) ABSTRACT

An interference fit assembly comprises a wick constructed of a porous polymer and a wall constructed of a polymer for interference engagement with the wick. The wick has a weight of 3.3 grams.

14 Claims, 7 Drawing Sheets

U.S. PATENT DOCUMENTS

| | | |
|---|---|---|
| 4,276,236 A | 6/1981 | Sullivan et al. |
| 4,294,778 A | 10/1981 | DeLuca |
| 4,323,193 A | 4/1982 | Compton et al. |
| 4,346,059 A | 8/1982 | Spector ............... 422/125 |
| 4,383,951 A | 5/1983 | Palson |
| 4,432,938 A | 2/1984 | Meetze, Jr. |
| 4,493,011 A | 1/1985 | Spector ................ 362/96 |
| 4,621,768 A | 11/1986 | Lhoste et al. ............ 239/44 |
| 4,660,764 A | 4/1987 | Joyaux et al. ............ 239/44 |
| 4,666,638 A | 5/1987 | Baker et al. |
| 4,695,435 A | 9/1987 | Spector |
| 4,707,338 A | 11/1987 | Spector |
| 4,739,928 A | 4/1988 | O'Neil |
| 4,743,406 A | 5/1988 | Steiner et al. |
| 4,857,240 A | 8/1989 | Kearnes et al. |
| 4,866,580 A | 9/1989 | Blackerby ............. 362/205 |
| 4,913,350 A | 4/1990 | Purzycki ................ 239/44 |
| 4,931,224 A | 6/1990 | Holzner, Sr. |
| 4,968,487 A | 11/1990 | Yamamoto et al. ....... 422/125 |
| RE33,864 E | 3/1992 | Steiner et al. |
| 5,095,647 A | 3/1992 | Zobele et al. ........... 43/125 |
| 5,114,625 A | 5/1992 | Gibson |
| 5,126,078 A | 6/1992 | Steiner et al. |
| 5,133,042 A | 7/1992 | Pelonis |
| 5,217,696 A | 6/1993 | Wolverton et al. ........ 422/121 |
| 5,222,186 A * | 6/1993 | Schimanski et al. ...... 392/395 |
| 5,223,182 A | 6/1993 | Steiner et al. |
| 5,342,584 A | 8/1994 | Fritz et al. |
| 5,370,829 A | 12/1994 | Kunze |
| 5,376,338 A | 12/1994 | Zlotnik |
| 5,547,616 A | 8/1996 | Dancs et al. |
| 5,647,053 A | 7/1997 | Schroeder et al. |
| 5,651,942 A | 7/1997 | Christensen ............ 422/125 |
| 5,662,835 A | 9/1997 | Collingwood |
| D386,974 S | 12/1997 | Wefler |
| D393,063 S | 3/1998 | Wefler |
| 5,891,400 A | 4/1999 | Ansari et al. ........... 422/125 |
| 5,909,845 A | 6/1999 | Greatbatch et al. |
| 5,919,423 A * | 7/1999 | Requejo et al. ......... 422/126 |
| 5,970,643 A | 10/1999 | Gawel, Jr. |
| 5,980,064 A | 11/1999 | Metroyanis ............. 362/194 |
| 6,017,139 A | 1/2000 | Lederer ................ 362/394 |
| 6,104,867 A | 8/2000 | Stathakis et al. ......... 392/403 |
| 6,106,786 A | 8/2000 | Akahoshi .............. 422/124 |
| 6,196,706 B1 | 3/2001 | Cutts ................. 362/392 |
| 6,241,161 B1 * | 6/2001 | Corbett ................ 239/58 |
| 6,354,513 B1 | 3/2002 | Millan |
| 6,354,710 B1 | 3/2002 | Nacouzi ............... 362/96 |
| 6,361,752 B1 | 3/2002 | Demarest et al. ......... 422/306 |
| 6,371,450 B1 | 4/2002 | Davis et al. |
| 6,416,242 B1 * | 7/2002 | Kaufmann ............. 401/198 |
| 6,454,425 B1 | 9/2002 | Lin ................... 362/96 |
| 6,484,438 B2 | 11/2002 | Matsunaga et al. ....... 343/129 |
| 6,555,068 B2 | 4/2003 | Smith |
| 6,567,613 B2 | 5/2003 | Rymer |
| 6,616,308 B2 | 9/2003 | Jensen et al. ............ 362/351 |
| 6,619,560 B1 * | 9/2003 | Chun .................. 239/44 |
| 6,862,403 B2 | 3/2005 | Pedrotti et al. .......... 392/395 |
| 6,899,280 B2 | 5/2005 | Kotary et al. |
| 6,938,883 B2 | 9/2005 | Adams et al. |
| 6,966,665 B2 | 11/2005 | Limburg et al. |
| 2002/0080601 A1 | 6/2002 | Meltzer ................ 362/96 |
| 2002/0093834 A1 | 7/2002 | Yu et al. ............... 362/565 |
| 2002/0136542 A1 | 9/2002 | He et al. ............... 392/395 |
| 2002/0136886 A1 | 9/2002 | He et al. .............. 428/313.5 |
| 2003/0007887 A1 | 1/2003 | Roumpos et al. .......... 422/1 |
| 2003/0053305 A1 | 3/2003 | Lin ................... 362/96 |
| 2003/0146292 A1 | 8/2003 | Schramm et al. |
| 2004/0065749 A1 | 4/2004 | Kotary et al. |
| 2004/0074982 A1 | 4/2004 | Kotary et al. |
| 2004/0141315 A1 | 7/2004 | Sherburne ............. 362/161 |
| 2004/0182949 A1 | 9/2004 | Duston et al. |
| 2004/0184969 A1 | 9/2004 | Kotary et al. |
| 2004/0246711 A1 | 12/2004 | Brenchley et al. ........ 362/161 |
| 2004/0257798 A1 | 12/2004 | Hart |
| 2004/0262419 A1 | 12/2004 | Kotary et al. |
| 2004/0262420 A1 | 12/2004 | Hansen et al. |
| 2004/0265189 A1 | 12/2004 | Schwarz |
| 2004/0265196 A1 | 12/2004 | Varanasi et al. .......... 422/305 |
| 2005/0053528 A1 | 3/2005 | Rymer |

FOREIGN PATENT DOCUMENTS

| | | | |
|---|---|---|---|
| DM | 054926 | 9/2000 | |
| EP | 0 882 459 | 12/1998 | |
| EP | 1 031 446 | 8/2000 | |
| EP | 1 270 021 | 1/2003 | |
| EP | 1 283 062 | 2/2003 | ............... 9/3 |
| EP | 1 283 062 A1 | 12/2003 | |
| GB | 2285579 | 7/1995 | |
| WO | WO95/10352 | 4/1995 | |
| WO | WO 01/02025 A1 | 1/2001 | |
| WO | WO 01/23008 A1 | 4/2001 | |
| WO | WO 02/30220 A1 | 4/2002 | |
| WO | WO 02/31413 A2 | 4/2002 | |
| WO | WO 03/013618 | 2/2003 | |
| WO | 1 392 368 | 10/2003 | |
| WO | WO03/086487 | 10/2003 | |
| WO | WO 2004/030708 | 4/2004 | |

OTHER PUBLICATIONS

"Luna Candles" http://www.epartyunlimited.com/luna-candles.html (print date 2005).

International Search Report and Written Opinion, Aug. 16, 2004, Appl. No. PCT/US04/008436.

International Search Report and Written Opinion, Aug. 16, 2004, Appl. No. PCT/US04/008437.

Schwarz U.S. Appl. No. 11/341,046, filed Jan. 25, 3006.

Kotary et al. U.S. Appl. No. 11/341,166, filed Jan. 27, 3006.

* cited by examiner

Table I

| wt (g) | $F_s$ |
|---|---|
| 3.156 | 7.07 |
| 3.16 | 7.3 |
| 3.162 | 7.93 |
| 3.171 | 7.14 |
| 3.177 | 7.83 |
| 3.193 | 7.01 |
| 3.201 | 7.2 |
| 3.211 | 6.76 |
| 3.218 | 7.19 |
| 3.222 | 7.66 |
| 3.224 | 7.21 |
| 3.227 | 7.33 |
| 3.229 | 7.06 |
| 3.242 | 7.19 |
| 3.243 | 7.11 |
| 3.251 | 7.53 |
| 3.269 | 7.4 |
| 3.271 | 7.57 |
| 3.281 | 7.54 |
| 3.286 | 7.62 |
| 3.29 | 7.11 |
| 3.293 | 7.8 |
| 3.3 | 7.22 |
| 3.377 | 8 |
| 3.528 | 8.15 |
| 3.59 | 8.33 |
| 3.629 | 8.34 |
| 3.643 | 7.66 |
| 3.655 | 8.41 |
| 3.755 | 7.72 |

Table II

| wt (g) | $F_1$ |
|---|---|
| 3.156 | 16.91 |
| 3.16 | 19.1 |
| 3.162 | 18.71 |
| 3.171 | 20.38 |
| 3.177 | 21.8 |
| 3.193 | 14.01 |
| 3.201 | 15.86 |
| 3.211 | 16.46 |
| 3.218 | 17.03 |
| 3.222 | 17.47 |
| 3.224 | 16.35 |
| 3.227 | 15.61 |
| 3.229 | 13.46 |
| 3.242 | 15.62 |
| 3.243 | 13.35 |
| 3.251 | 18.2 |
| 3.269 | 15.97 |
| 3.271 | 15.59 |
| 3.281 | 19.89 |
| 3.286 | 17.54 |
| 3.29 | 28.31 |
| 3.293 | 20.35 |
| 3.3 | 17.86 |
| 3.377 | 15.92 |
| 3.528 | 20.05 |
| 3.59 | 19.07 |
| 3.629 | 20.45 |
| 3.643 | 19.36 |
| 3.655 | 19.87 |
| 3.755 | 19.85 |

WICK ASSEMBLY FOR DISPENSING A VOLATILE LIQUID FROM A CONTAINER AND METHOD OF ASSEMBLING SAME

FIELD OF THE INVENTION

The application relates to dispensing systems for volatile liquids and, more particularly, to a dispensing system incorporating a porous wick.

SUMMARY OF THE INVENTION

According to one aspect of the invention, an interference wick assembly for dispensing a volatile liquid from a container includes a porous high density polymer wick and a plug for securement within an opening into the container. The plug includes a tapered receiver tube defining a second opening through the plug and a ridge along an inner surface of the tube. A portion of the second opening has a first dimension less than a dimension of the wick. The wick is secured within the tube by an interference fit with the ridge, and the wick has a density sufficient to develop a removal force of at least 7.22 pounds two weeks after securement within the tube.

According to another aspect of the invention, an interference fit wick assembly for dispensing a volatile liquid from a container includes a porous wick composed of high density polymer and having a first density and a polymeric wall defining an opening having a dimension less than a dimension of the wick. The wick is retained within the opening by a separation force caused by the interference fit, and the first density is selected such that the separation force is at least as great as a first force. The wall includes a generally frustoconical receiving member defining the opening, an insertion end having a first diameter, and a retention end having a second diameter. The first diameter is greater than the wick dimension, and the second diameter is less than the wick dimension.

According to yet another aspect of the invention, a method of assembling a wick assembly for dispensing a volatile liquid from a container includes the step of providing a porous wick. The wick is composed of high density polymer and has a first density. The method further includes the step of providing a generally frustoconical wall defining an opening. The wall is of a high density polyethylene and has an inner annular ridge. The opening has a dimension less than a dimension of the wick. The method also includes the step of inserting the wick into the opening. The first density is selected such that a separation force is at least as great as a first force.

These and other aspects of the invention will become apparent upon consideration of the detailed description and the drawings.

DETAILED DESCRIPTION OF THE INVENTION

Figure 1:
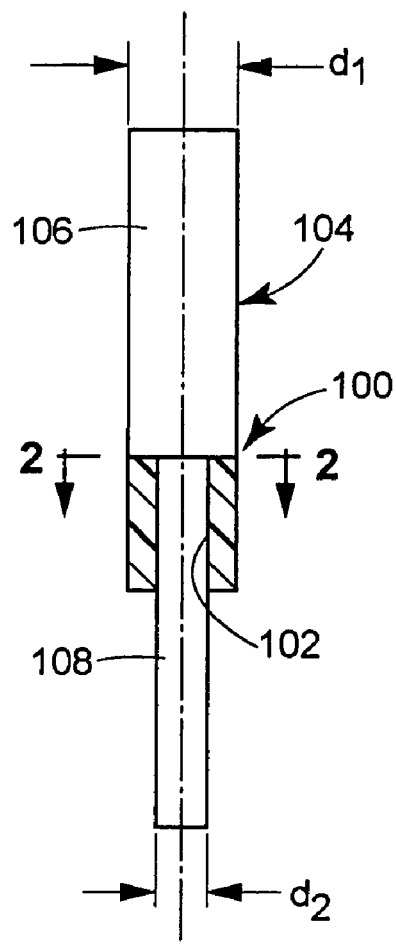
FIG. 1 is a cross sectional view showing one embodiment of an interference fit assembly according to the present invention.

Referring to FIG. 1, interference fit assembly 100, in one example, comprises wall 102 and wick 104. An interference fit couples wall 102 and wick 104 together. As shown in FIG. 1, wick 104 comprises a generally cylindrical first portion 106 having a first diameter $d_1$ and a generally cylindrical second portion 108 having a second diameter $d_2$. Second portion 108 extends through an opening (not shown) of wall 102. FIG. 1 depicts diameters $d_1$ and $d_2$ such that first diameter $d_1$ is greater than second diameter $d_2$. Alternatively, $d_1$ is less than $d_2$, or $d_1$ and $d_2$ are the same size.

Figure 2:
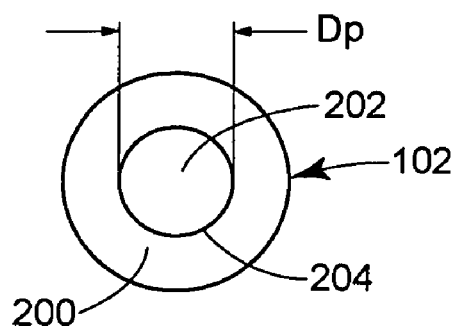
FIG. 2 is a cross sectional view of the interference fit assembly of FIG. 1 taken along line 2-2 in FIG. 1.

FIG. 2 provides a top view of wall 102 taken along line 2-2 in FIG. 1. Wall 102 in one example forms an annular member 200. Annular member 200 includes an opening 202. Annular member has an interior diameter $D_p$ which is defined as the diameter of opening 202. $D_p$ is less than diameter $d_2$ of the second portion 108 of wick 104. In one example, diameter $d_2$ is 6.5% greater than $D_p$. In another example, diameter $d_2$ does not exceed approximately 12% of $D_p$.

Figure 3:
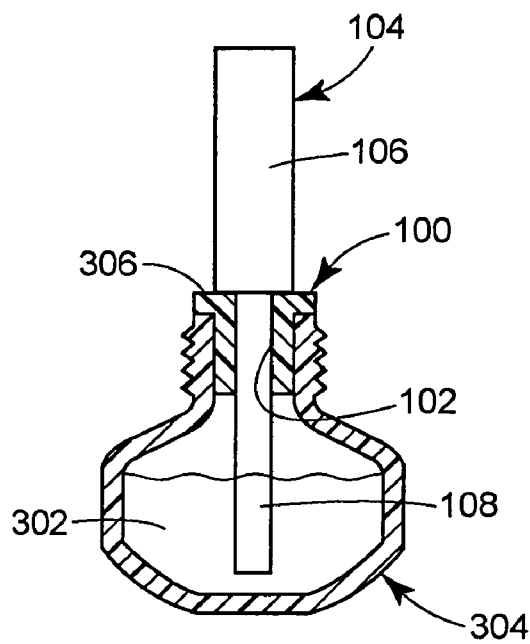
FIG. 3 is a cross sectional view of the interference fit assembly of FIG. 1 incorporated into a container for a volatile liquid.
Figure 4:
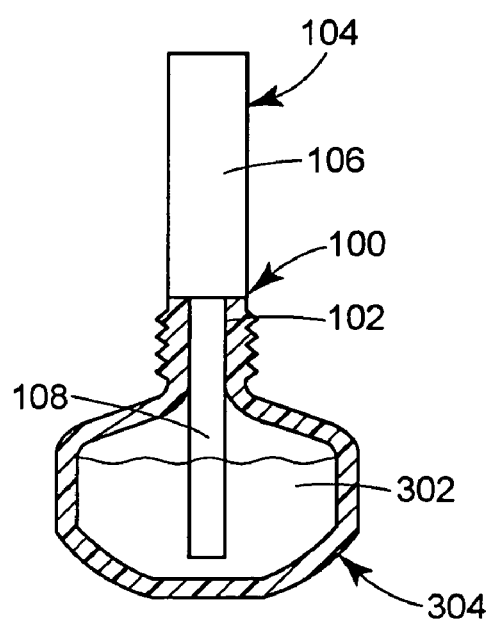
FIG. 4 is a cross sectional view showing a second embodiment of an interference fit assembly according to the present invention.

Referring to FIGS. 3 and 4, wick 104 is utilized to draw a liquid 302 from a container 304. Liquid 302, in one example, is a volatile liquid, which emits a fragrance, and container 304 is a fragrance bottle. Wick first portion 106 extends outside container 304 for immersion into either ambient air or a forced air stream. Wick second portion 108 is in communication with liquid 302. Accordingly, liquid 302 is drawn from container 304 by wick second portion 108 and deposited into the ambient air by wick first portion 106.

FIGS. 3 and 4 disclose two embodiments for utilizing interference fit 100 to connect wick 104 to container 304. In a first embodiment, shown in FIG. 3, wall 102 is incorporated into plug member 306. Plug member 306 is adapted to be received and secured to container 304. Plug member 306 is secured to container 304 through means, such as an interference fit, molding, adhesive, etc. In a second embodiment, shown in FIG. 4, wall 102 is incorporated directly into container 304. The disclosure of the two embodiments in FIGS. 3 and 4 is for illustrative purposes only and should not be used to limit the scope of the application to the two embodiments.

Referring now to FIGS. 1 and 2, it should be noted that in addition to securing wall 102 and wick 104 together, interference fit assembly 100 also forms a seal to prevent leakage of liquid from the container in which wick 104 is inserted. Thus, wick second portion 108 conforms to the shape of opening 202 and substantially abuts the entire interior surface 204 of annular member 200. In the example shown, wick second portion 108 has a generally cylindrical shape to conform to the circular shape of opening 202. In another example, opening 202 and wick could be shaped differently; for example, if achieving a seal between wick 104 and the container in which it is inserted is not of importance.

In another example, wick 104 and/or opening 202 have other geometric shapes, such as hexagonal, rectangular, triangular, elliptical, etc. Detailed descriptions of wick structures are provided in co-pending patent applications having U.S. Ser. Nos. 10/266,512; 10/266,798; and 10/266,546, which are hereby incorporated by reference.

Wall 102 is formed from a thermoplastic material having the processing characteristics and dimensional stability needed to enable predetermined interference fit dimensional tolerances to be achieved and maintained. In one example, wall 102 is formed from a high density polyethylene, such as for example Alathon® H 5520 from Equistar Chemicals, LP of Houston, Tex.

Wick 104 in one example is made from material that is appropriate for its function. For example, in FIGS. 3 and 4, wick 104 is utilized to deliver liquid 302 from container 304 into ambient air or a forced air stream. Accordingly, wick 104 is chosen to have a predetermined range of void volume and/or pore size appropriate for providing this function. Void volume and pore size can be determined by any standard test for determining void volume and pore size distribution. For example, mercury porosimetry provides information on void volume and pore size distribution for rigid wicks. The material of wick 104 also has the processing characteristics and dimensional stability needed to enable predetermined interference fit dimensional tolerances to be achieved and maintained. In one example, wick 104 is a polymeric wick made of sintered ultra high molecular weight polyethylene (UHMW-PE). In another example, wick 104 is comprised of a blend of UHMW-PE in particle form, which is developed to meet the target pore characteristics of the wick 104. An exemplary wick can be obtained from MicroPore Plastics Inc. of Stone Mountain, Ga.

Figure 5:
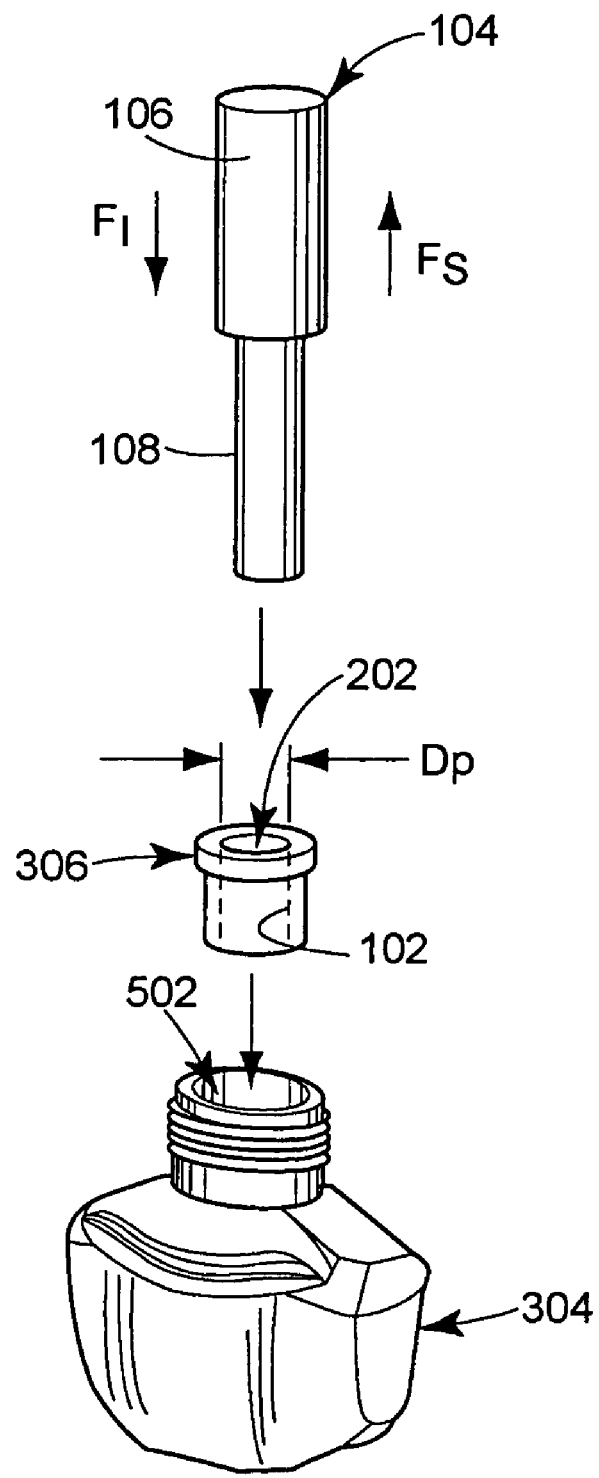
FIG. 5 is an exploded perspective view of the interference fit assembly and container of FIG. 3.

The material for wick 104 is also chosen to effect a specific strength of the interference fit between wall 102 and wick 104. FIG. 5 shows an exploded view of the first embodiment of interference fit assembly 100. Wick 104 is inserted into opening 202 of plug member 306. Plug member 306 is inserted into opening 502 of container 304. Because Diameter $d_2$ of wick second portion 108 is larger than diameter $D_p$ of opening 202, an interference fit is created. To insert wick 104 through opening 202, however, an insertion force $F_I$ is applied to wick 104 in the direction shown. For wick 104 to be removed from opening 202, a separation force $F_s$ or extraction force needs to be applied to wick 104 in the direction shown. For many applications, however, the manufacturer may not want wick 104 to be easily removed from opening 202. For example, if interference fit assembly 100 were used as part of an air freshener, the manufacturer may not want children to be able to remove wick 104 because to do so would result in the spilling of liquid in their vicinity. Therefore, the manufacture may want the separation force $F_s$ to be strong enough to prevent this from happening. The Applicants have discovered that both $F_I$ and $F_s$ are a function of the weight of wick 104. In particular, the density of wick 104 along and near the region of wick 104 that abuts wall 102 affects separation force $F_s$. The higher the density of wick 104, the greater force that is required to both insert wick 104 into opening 202 and remove wick 104 from opening 202.

Still referring to FIG. 5, after wick 104 is inserted into opening 202, a period of stress relaxation occurs. Stress relaxation occurs in the materials of both wall 102 and wick 104 along and proximate the region of contact between wall 102 and wick 104. The stress relaxation reduces the bearing force between wall 102 and wick 104 and thus $F_s$ decreases as a result of stress relaxation. Therefore, when determining when manufacturing interference fit assembly 100 to have a particular separation force $F_s$, the manufacture must take into account the effects of stress relaxation. The Applicants have found that a period of about two weeks is sufficient to allow the effects of stress relaxation to occur. After two weeks, separation force $F_s$ has generally stabilized.

Figure 6:
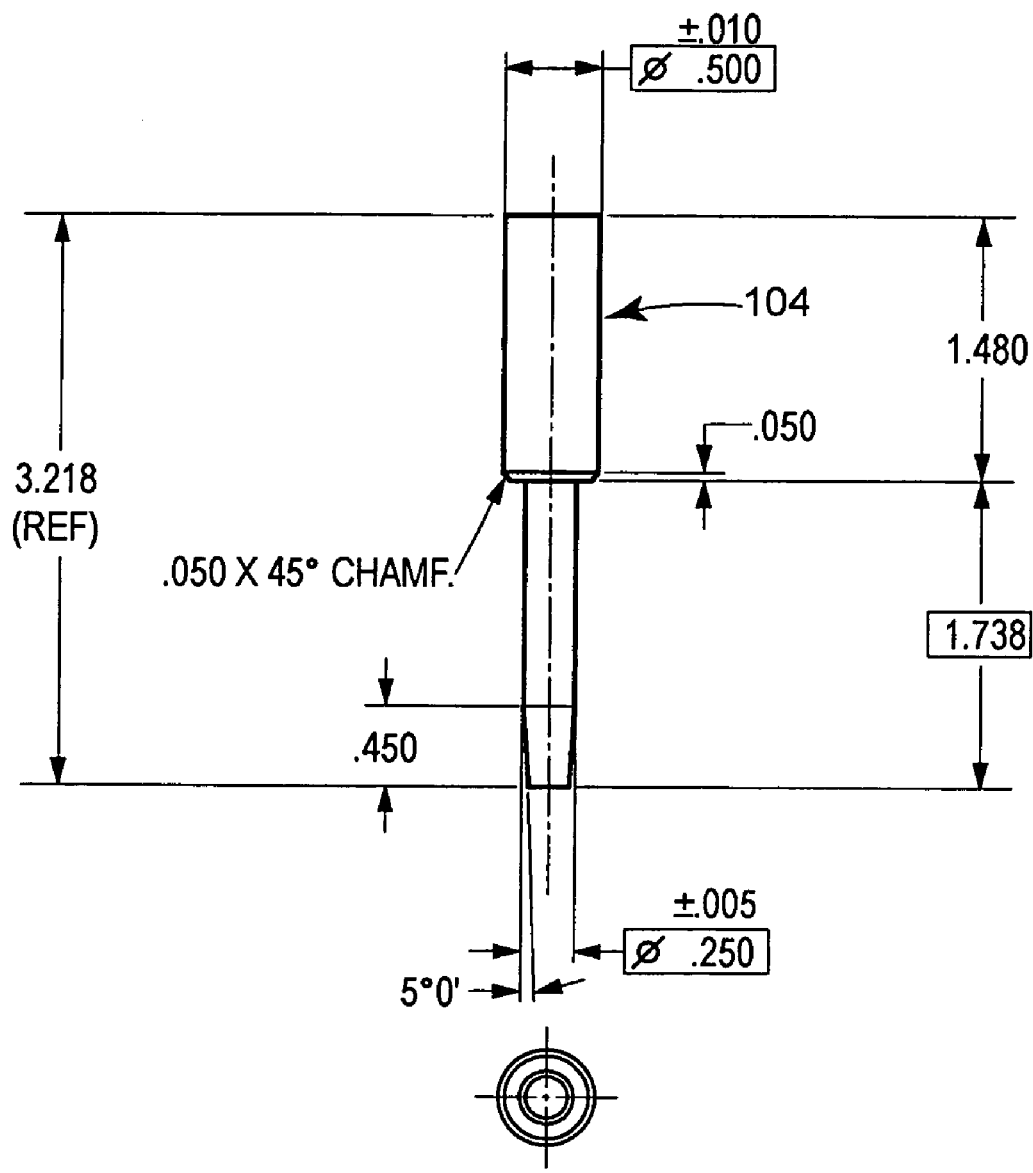
FIG. 6 is a schematic drawing showing the dimensions and shape of an exemplary wick.
Figure 7:
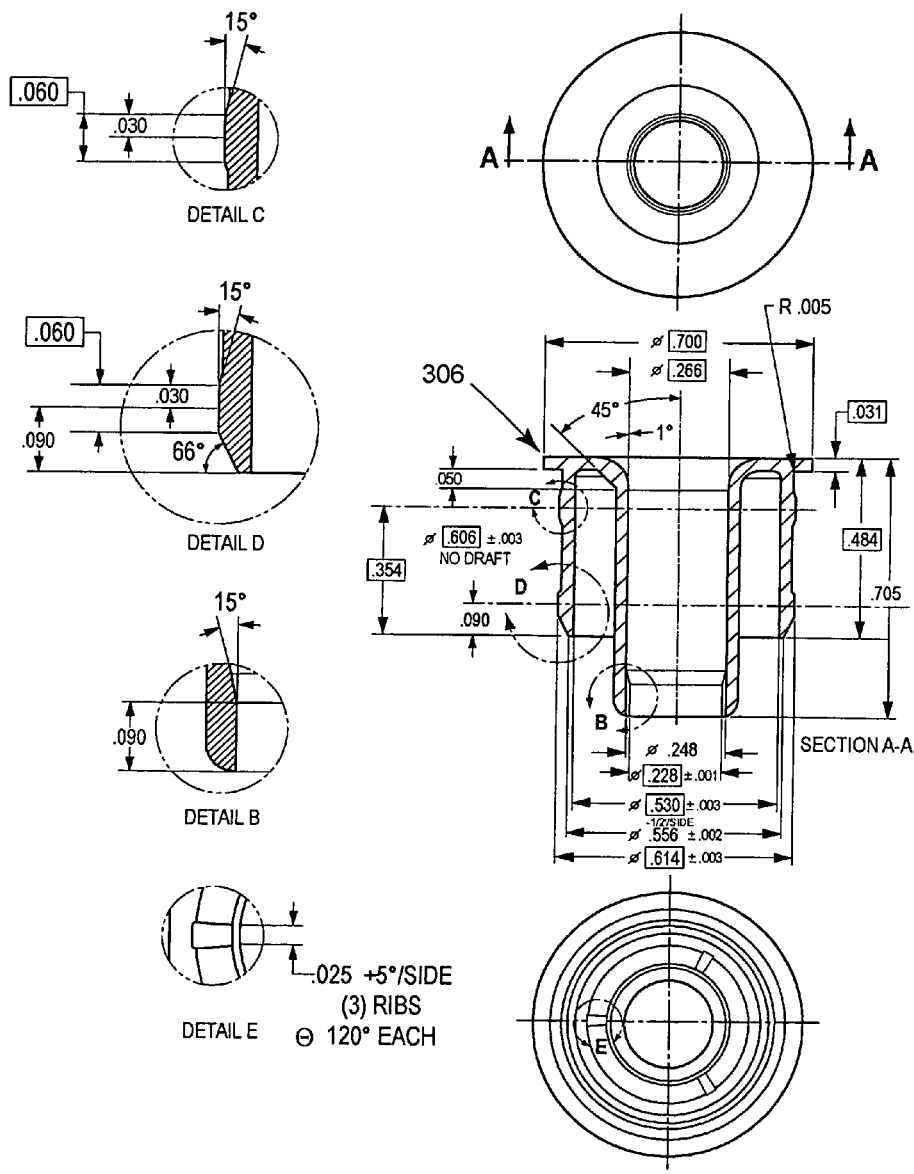
FIG. 7 is a group of drawings showing dimensions and shape of the plug member 306 of FIG. 3.
Figures 8A, 8B:
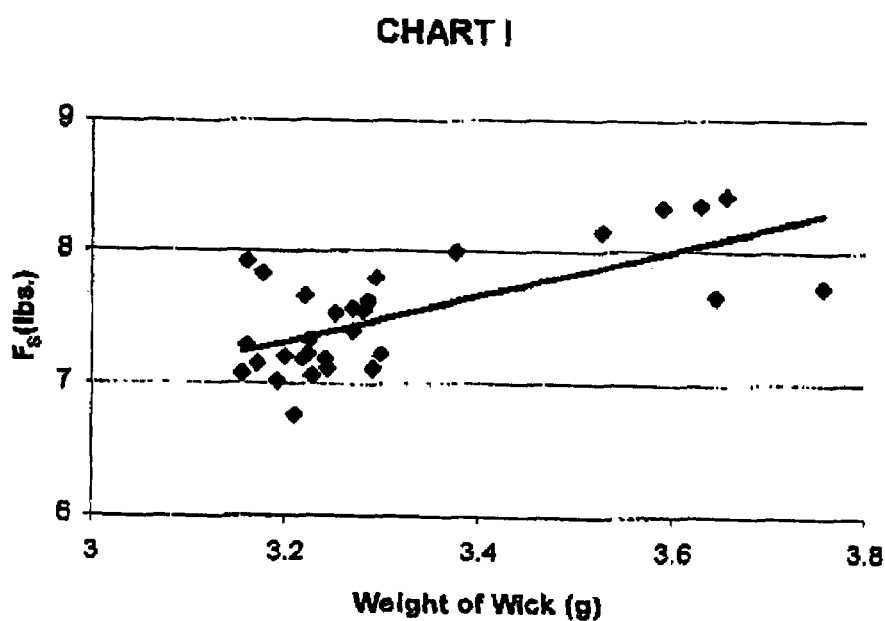
FIGS. 8A and 8B are a table and chart, respectively, showing the effect of increasing weight on separation force $F_3$.

FIGS. 8A and 8B, which include Table I and Chart I, respectively, show the effect that increasing the weight, for a given volume of wick 104, has on the separation force F, for a wall and wick after a period of about two weeks.[1] In other words, Table I and Chart I show the effect that increasing the density of wick 104 has on separation force $F_s$. The wall 102 was made of approximately 0.9 ± 0.05 g of injection molded high density polyethylene. Wall 102 was incorporated into plug member 306 and plug member 306 was inserted into container 304 as shown in FIG. 3. The dimensions of wall 102, plug member 306, and wick 104 are provided in FIGS. 6 and 7. It should be noted that the dimensions provided for wall 102 and wick 104 are for illustrative purposes only. Wall 102 and wick 104 could be made larger or smaller. Provided that an interface fit is generated between wall 102 and wick 104, the separation force $F_s$ will increase as the density of wick 104 increases for a constant density of wall 102. The density of wick 104 can be determined by calculating volume of wick 104 using the dimensions shown in FIG. 6.

[1] For the weights 3.643, 3.755, 3.528, 3.629, 3.590, and 3.655 wick 104 was not separated from wall 102. Rather, plug member 306 separated from container 304. Accordingly, these entries list the force at which plug member was removed from container 304.

Figures 9A, 9B:
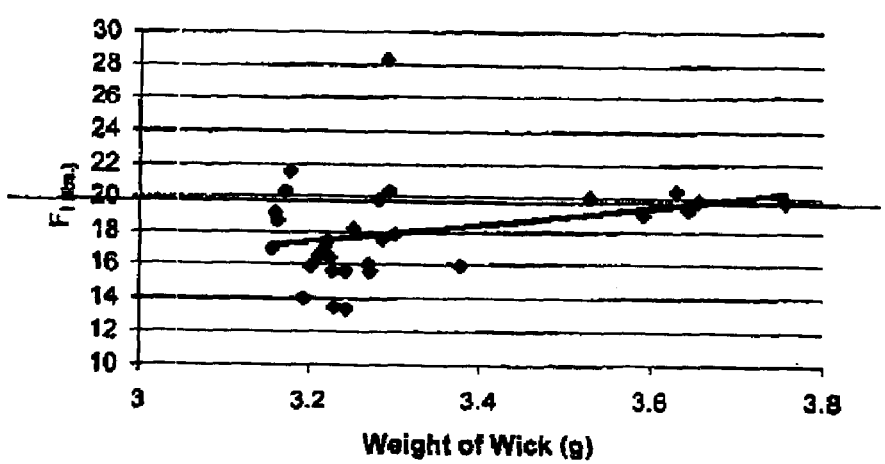
FIGS. 9A and 9B are a table and chart, respectively, showing the effect of increasing weight on insertion force.

FIGS. 9A and 9B. which include Table II and Chart II, respectively, demonstrate the effect that increasing the weight (and thereby density) of wick 104 has on insertion force for the same wall and wick as in Table I and Chart I. The tables and charts demonstrate that the higher the weight of wick 102, the greater the insertion force $F_I$ and the greater the separation force $F_s$ after stress relaxation.

INDUSTRIAL APPLICABILITY

The present invention provides an interference fit assembly incorporation into a container for a volatile liquid. The assembly is formed by a porous wick and a wall joined so as to generate an interference fit. The assembly forms a seal at an opening of the container to prevent leakage of the volatile liquid from the container. To help ensure that the seal remains secured in the opening of the container, the assembly is constructed such that at least a minimum threshold force is required to separate the wick from the wall. To this end, the materials and dimensions of the wick and wall are specified so as to provide a high initial engagement force between the wick and wall, and to provide maximum resistance to stress relaxation at the wick-wall interface.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

The invention claimed is:

1. An interference wick assembly for dispensing a volatile liquid from a container, comprising:
   a porous high density polymer wick;
   a plug for securement within an opening into the container, wherein the plug includes a tapered receiver tube defining a second opening through the plug and a ridge along an inner surface of the tube, and wherein a portion of the second opening has a first dimension less than a dimension of the wick;
   wherein the wick is secured within the tube by an interference fit with the ridge, and wherein the wick has a density sufficient to develop a removal force of at least 7.22 pounds two weeks after securement within the tube.

2. The wick assembly of claim 1 wherein the wick is formed from ultra-high molecular weight polyethylene.

3. The wick assembly of claim 1 wherein the tapered receiver tube is formed from high density polyethylene.

4. The wick assembly of claim 1 wherein the ridge comprises an annular member and the wick has a generally cylindrical shape.

5. The wick assembly of claim 4 wherein an interior diameter of the annular member is less than a diameter of the wick.

6. The wick assembly of claim 5 wherein the diameter of the wick is at least 6.5% greater than the interior diameter of the annular member.

7. The wick assembly of claim 5 wherein the diameter of the wick does not exceed by approximately 12% the interior diameter of the annular member.

8. The wick assembly of claim 4 wherein the receiver tube engages the first opening into the container.

9. The wick assembly of claim 8 wherein the diameter of the first opening into the container is smaller than an exterior diameter of the receiver tube.

10. A method of assembling a wick assembly for dispensing a volatile liquid from a container, wherein the method comprises the steps of:
    providing a porous wick composed of high density polymer and having a first density;
    providing a generally frustoconical wall defining an opening, wherein the opening has a dimension less than a dimension of the wick, wherein the wall is of a high density polyethylene and has an inner annular ridge, and wherein the first density is selected such that a separation force is at least as great as a first force; and
    inserting the wick into the opening.

11. The method of claim 10 wherein the step of providing a wick includes the step of providing the wick formed of an ultra high molecular weight polyethylene.

12. An interference fit wick assembly for dispensing a volatile liquid from a container, wherein the wick assembly comprises:
    a porous wick composed of high density polymer and having a first density; and
    a polymeric wall defining an opening having a dimension less than a dimension of the wick;
    wherein the wick is retained within the opening by a separation force caused by the interference fit; and
    wherein the first density is selected such that the separation force is at least as great as a first force; and
    wherein the wall comprises a generally frustoconical receiving member defining the opening and including an insertion end having a first diameter and a retention end having a second diameter; and
    wherein the first diameter is greater than the wick dimension and the second diameter is less than the wick dimension.

13. The wick assembly of claim 12, wherein the generally frustoconical receiving member further comprises an inner annular ridge adjacent to the retention end.

14. The wick assembly of claim 13, wherein the wall further comprises an annular skirt spaced radially outwardly from the receiving member and sized to have an interference fit with an inner surface of an opening in the container.

* * * * *